United States Patent [19]

Larkins et al.

[11] 4,374,070

[45] Feb. 15, 1983

[54] PREPARATION OF ACETIC ANHYDRIDE

[75] Inventors: Thomas H. Larkins; Stanley W. Polichnowski; Gerald C. Tustin, all of Kingsport, Tenn.; David A. Young, Baton Rouge, La.

[73] Assignee: Eastman Kodak Company, Rochester, N.Y.

[21] Appl. No.: 209,350

[22] Filed: Nov. 21, 1980

[51] Int. Cl.$^3$ .............................................. C07C 51/54
[52] U.S. Cl. .................................................... 260/549
[58] Field of Search ........................................ 260/549

[56] References Cited

U.S. PATENT DOCUMENTS

| | | |
|---|---|---|
| 3,579,566 | 5/1971 | Fenton . |
| 4,046,807 | 9/1977 | Kruckertz ............................ 260/549 |
| 4,252,741 | 2/1981 | Porcelli et al. ....................... 260/549 |

FOREIGN PATENT DOCUMENTS

| | | |
|---|---|---|
| 819455 | 3/1975 | Belgium . |
| 52-3926 | 1/1977 | Japan . |
| 761482 | 11/1977 | South Africa . |
| 2013184 | 12/1978 | United Kingdom . |

OTHER PUBLICATIONS

Derwent Abstracts, 75-47921 Japan, Showa, Denkokk, Apr. 28, 1975.
Derwent Abstracts, 75-47922 Japan, Showa, Denkokk, Apr. 28, 1975.
Chem. Tech., 1971, p. 600, Roth et al., "Low Pressure Process for Acetic Acid via Carbonylation".

Primary Examiner—Alan Siegel
Attorney, Agent, or Firm—J. Frederick Thomsen; Daniel B. Reece, III

[57] ABSTRACT

The preparation of acetic anhydride by the carbonylation of methyl acetate in the presence of rhodium, an iodine compound and lithium at elevated temperatures and pressures is improved by the inclusion of about 2 to 7 volume percent hydrogen in the gas fed to the carbonylation reactor. The presence of hydrogen suppresses tar formation and increases reaction rate.

4 Claims, No Drawings

PREPARATION OF ACETIC ANHYDRIDE

This invention concerns an improved process for the manufacture of acetic anhydride by the carbonylation of methyl acetate.

It has long been known that acetic acid and acetic anhydride can be prepared by the carbonylation of methanol and methyl acetate, respectively. For example, Reppe et al. in U.S. Pat. Nos. 2,729,651 and 2,789,137 disclose processes for carbonylating methanol and methyl acetate using nickel and cobalt catalysts. The use of such catalysts, however, required extremely high pressures, e.g. as high as 10,000 psi, an obviously undesirable feature of the processes. Paulik et al., in U.S. Pat. No. 3,769,329 disclose that moderate pressures can be employed in the synthesis of acetic acid by the carbonylation of methanol by substituting rhodium for the catalysts used by Reppe et al. Paulik et al. also disclose that a halogen component such as methyl iodide is an essential ingredient in the rhodium-containing catalyst system.

The use of catalyst systems comprising rhodium and an iodine compound in the preparation of acetic anhydride by the carbonylation of methyl acetate has been reported in the patent literature. See, for example, Belgian Pat. No. 819,455, British Published Patent Application No. 2,013,184, Japanese Published Patent Applications Nos. 75-47921 and 75-47922 and U.S. Pat. Nos. 3,927,078 and 4,046,807. Those publications also disclose that the reaction rate can be increased if the catalyst system contains a promoter such as certain amines, phosphines and inorganic materials such as lithium compounds. The use of amines and phosphines, particularly under conditions giving high space-time yields, causes formation of tars which cannot be handled in a continuous process. The use of lithium compounds, such as lithium iodide or lithium acetate, does not entirely avoid the formation of tar but the tar that is formed is not unmanageable.

Tar formation, which is essentially unavoidable in the carbonylation of methyl acetate, increases as reaction conditions, such as temperature and pressure, are increased to obtain a desirably high space-time yield such as 400 g./l./hr. or greater. It is known (U.S. Pat. No. 4,046,807) that the inclusion of hydrogen in the gas feed to the carbonylation reactor in a system employing triphenylphosphine can suppress tar formation. The presence of hydrogen in the gas feed causes the production of ethylidene diacetate (Belgian Pat. No. 839,321) in addition to acetic anhydride, thereby requiring a means for the disposition of the former. The inclusion of hydrogen in the gas feed also increases the formation of methane. It therefore is important to minimize the amount of hydrogen used in order that overall yields of acetic anhydride are not decreased.

Our invention is an improvement in the preparation of acetic anhydride by the liquid phase carbonylation of methyl acetate in the presence of rhodium, an iodine compound and lithium at elevated pressure and temperature wherein a feed mixture containing methyl acetate is continuously fed to a carbonylation reactor and a reaction mixture containing acetic anhydride is continuously removed wherein about 2 to 7 volume percent of the gas fed to the reactor is hydrogen. We have discovered that the addition of hydrogen not only suppresses tar formation but increases significantly the reaction rate both in terms of methyl acetate conversion and acetic anhydride production. It also has been found that in continuous operation, at least under certain conditions, in which hydrogen is being fed to the carbonylation reactor that when the hydrogen feed is stopped the rate of methyl acetate carbonylation will decrease to the point that the process will shut down. In contrast to our discovery, literature [Roth et al., Chem. Tech., 600 (1971)] on the rhodium-catalyzed carbonylation of methanol to acetic acid indicates that high levels of hydrogen have no effect on the reaction.

The role of hydrogen in our process has been determined by infrared spectroscopic monitoring of an ongoing reaction. Using a batch autoclave coupled with a high-temperature, high-pressure infrared cell, the rhodium complexes present during the reaction have been observed. In the absence of hydrogen feed the major rhodium species in solution at 175° C. and 800 psig is trans-$Rh(CO)_2I_4\ominus$ as evidenced by the metal carbonyl absorption at 2090 cm$^{-1}$. A smaller amount of cis-$Rh(CO)_2I_2\ominus$ is also present under these conditions as indicated by the absorptions at 2056 and 1983 cm$^{-1}$ for the carbonyls bonded to rhodium. The addition of hydrogen to the reaction at 175° C. and 800 psig results in the rapid disappearance of the infrared absorption at 2090 cm$^{-1}$ for trans-$Rh(CO)_2I_4\ominus$. At the same time, the absorptions for cis-$Rh(CO)_2I_2\ominus$ at 2056 and 1983 cm$^{-1}$ dramatically increase in intensity. The observed transformation of trans-$Rh(CO)_2I_4\ominus$ to cis-$Rh(CO)_2I_2\ominus$ is also accompanied by a substantial increase in the rate of formation of $Ac_2O$. On the basis of the infrared spectroscopic measurements it is apparent that the addition of hydrogen in our process increases the concentration of the active catalyst, cis-$Rh(CO)_2I_2\ominus$.

The minimum amount of hydrogen that gives a significant effect is about 2 volume percent based on the total carbon monoxide and hydrogen fed. The use of greater than about 7 volume percent hydrogen is not desirable since it does not significantly improve either the suppression of tar formation or the rate of acetic anhydride formation. The preferred amount of hydrogen fed is about 3 to 6 volume percent based on the total amount of hydrogen and carbon monoxide fed to the carbonylation reactor.

In the practice of the process, the feed to the reactor is such as to maintain within the reaction mixture (1) about 250 to 1300 ppm, preferably about 500 to 1000 ppm, Rh, (2) about 175 to 5000 ppm, preferably about 1500 to 3700 ppm, lithium and (3) about 7 to 35 weight percent methyl iodide. The remainder of the reactor contents consists mostly of methyl acetate reactant and acetic anhydride product with minor amounts of by-products such as ethylidene diacetate and acetone. The reactor feed optionally may contain a solvent such as acetic acid, e.g. in an amount that will maintain about 5 to 40 weight percent in the reaction mixture. In a liquid take-off system, the catalyst components, i.e. the rhodium, lithium and iodine as methyl iodide, are recovered from the reactor effluent and are recycled. When necessary, fresh rhodium, as rhodium chloride, rhodium acetate or other rhodium containing compound, and lithium, as lithium hydroxide, lithium iodide, lithium acetate or other lithium-containing compound are added to the catalyst recycle. The fresh rhodium and lithium can be conveniently added as a solution in acetic acid. When the iodine needs to be supplemented it may be added to the system as iodine ($I_2$), as methyl iodide or, at least in part, as lithium iodide. In a vapor take-off system, all or essentially all of the rhodium and lithium catalyst components remain in the reactor and thus, the risk of their depletion from the process is reduced considerably.

The methyl acetate fed to the reactor consists primarily of fresh methyl acetate, which should be essentially anhydrous, and some recycled material. The feed may also contain recycled acetic anhydride although it is advantageous to add methanol to any recycled anhydride to convert the latter to methyl acetate feedstock.

The process may be carried out at elevated temperatures and pressures in the range of about 160° to 220° C. and about 300 to 1200 psig. The particular temperature and pressure that are employed will depend on a number of factors such as the amounts of the three catalysts components that are used, by-product formation, the design of the process system and the space-time yield desired.

The invention is further illustrated by the following examples.

EXAMPLE 1

The reactor consists of a lower section of five feet, five inches of two-inch Sch. 40 pipe, a middle section of six feet, one inch of one-inch Sch. 40 pipe and six feet of one-half inch Sch. 40 pipe. Total reactor volume is 4.95 liters. A gas mixture of carbon monoxide and 5 volume percent hydrogen is fed through a gas sparger at the bottom of the reactor. Through a reactor feed line, located above the sparger, is fed a mixture containing methyl acetate, acetic acid, acetic anhydride, methyl iodide, lithium and rhodium at an average rate of about 12,600 grams/hour. The reactor contents overflow from the top of the reactor to a reactor separator pot where some of the unreacted carbon monoxide and other gases are separated from the liquid and purged from the system. The liquid from the reactor separator pot passes through a valve which reduces the pressure from about 750 psig to 10–20 psig. The liquid passes through a flash evaporator, wherein about 80–90% of the material is vaporized and enters an evaporator separator pot (about 1 psig) wherein the vapor and liquid are separated. The liquid, which consists mainly of acetic acid and acetic anhydride in which the rhodium and lithium catalyst components are dissolved along with minor amounts of methyl iodide and methyl acetate, is recycled to the reactor. The vapors from the evaporator separator pot are fed to a column in which the temperature is maintained at about 140° C. at the base and about 100° C. at the top. Crude acetic anhydride suitable for further refining is removed from the lower portion of the column. The low boilers (methyl acetate, methyl iodide and some acetic acid) are taken overhead and fed to a low boiler blend tank to which makeup methyl acetate is also fed. The contents of the blend tank are continuously fed to the reactor feed line.

Using the above-described system, acetic anhydride was produced by the carbonylation of methyl acetate at about 190° C. and 750 psig. Over the course of 80 hours of continuous operation samples of the reactor separator pot liquid and the reactor feed periodically were analyzed and the conversion of methyl acetate (methyl acetate fed minus methyl acetate in the separator pot liquid divided by methyl acetate fed) and the space-time yield (STY, in grams/liter/hours) were determined. The data thus accumulated is shown in Table I. The hydrogen in the gas feed was stopped at hour 245 and was resumed at hour 267.

The data of Table I show that discontinuing the hydrogen feed to the carbonylation reactor has a substantial effect on production rate, i.e. space-time yield.

TABLE I

| Operating Time, Hours | Reactor Separator Pot Underflow Composition | | | | | | Reactor Feed | | Conversion % | Space Time Yield (8 Hour Average) |
|---|---|---|---|---|---|---|---|---|---|---|
| | Rh ppm | Li ppm | MeI % | MeOAc % | HOAc % | $Ac_2O$ % | MeOAc % | $Ac_2O$ % | | |
| 219 | 496 | 1941 | 17.7 | 28.3 | 17.6 | 34.7 | 44.6 | 15.9 | 37 | |
| 223 | | | — | — | — | — | 45.9 | 20.8 | — | |
| 227 | 504 | 3121 | 16.0 | 16.9 | 16.7 | 46.8 | 42.5 | 21.3 | 60 | 650 |
| 231 | | | 15.5 | 17.0 | 20.8 | 43.4 | 41.0 | 19.4 | 59 | |
| 235 | 790 | 3587 | 15.4 | 8.6 | 33.2 | 39.4 | 27.3 | 21.9 | 68 | 606 |
| 243 | 593 | 3206 | 19.1 | 9.9 | 23.3 | 41.9 | 25.3 | 24.1 | 61 | 482 |
| 247 | | | 27.2 | 17.8 | 27.3 | 28.9 | 20.7 | 13.5 | 14 | |
| 251 | 482 | 2802 | 21.0 | 21.4 | 26.8 | 26.3 | 37.4 | 11.9 | 43 | 254 |
| 255 | | | 19.7 | 22.4 | 30.3 | 25.7 | 45.9 | 9.5 | 51 | |
| 259 | 388 | 1634 | 25.8 | 15.4 | 32.9 | 21.8 | 38.4 | 6.9 | 60 | 292 |
| 267 | 474 | 2451 | 22.2 | 22.8 | 33.0 | 20.3 | 30.1 | 9.0 | 24 | 223 |
| 271 | | | 21.0 | 16.5 | 23.3 | 34.9 | 31.0 | 15.9 | 47 | |
| 275 | 450 | 2268 | 20.4 | 14.8 | 20.0 | 34.9 | 29.7 | 18.7 | 50 | 401 |
| 279 | | | 21.0 | 18.6 | 23.1 | 34.1 | 35.0 | 15.5 | 47 | |
| 283 | 469 | 2375 | 21.9 | 17.5 | 22.9 | 34.0 | 45.7 | 13.2 | 62 | 435 |
| 291 | 905 | 3955 | 23.4 | 24.1 | 19.9 | 31.3 | 49.7 | 8.8 | 52 | 389 |
| 295 | | | 18.6 | 24.9 | 18.9 | 36.3 | 37.5 | 16.2 | 34 | |
| 299 | 408 | 2216 | 16.7 | 17.8 | 25.9 | 35.3 | 30.9 | 17.4 | 42 | 358 |

EXAMPLE 2

Four runs in which varying amounts of hydrogen are fed to the carbonylation reactor was carried out in the apparatus described in Example 1 except that the reactor consists of the five feet, six inches of Sch. 40 pipe having a volume of 3.5 liters. The reactor temperature is about 190° C., the pressure about 750 psig and reactor feed rate about 12,600 grams/hour over the course of each run. In Table II are set forth average values for each run, the composition of the reactor feed stream (weight percent), the rhodium and lithium (ppm) present in the system, the amount of hydrogen fed (volume percent of the total gas fed), the acetic anhydride space-time yield (STY; grams/liter/hour) and the weight ratio of ethylidenediacetate to acetic anhydride produced. The duration of the first run is 64 hours, the second 65.5 hours, the third 73 hours and the fourth 34 hours.

In Runs 1–3, high space-time yields are obtained although the higher concentrations of hydrogen result in the formation of significant amounts of ethylidenediacetate. In Run 4, essentially no ethylidenediacetate is formed but the space-time yield is decreased considerably by the use of 1.2 volume percent hydrogen in the gas feed.

TABLE II

| | | | Reactor Feed Composition | | | | | | |
|---|---|---|---|---|---|---|---|---|---|
| Run | MeI | MeOAc | HOAc | Ac$_2$O | EDA | Rh | Li | H$_2$ | STY | EDA:Ac$_2$O |
| 1 | 15.0 | 50.4 | 20.4 | 12.8 | 0.38 | 607 | 2098 | 6.25 | 573 | 0.0131 |
| 2 | 14.8 | 51.9 | 16.8 | 15.9 | 0.39 | 696 | 1977 | 4.33 | 564 | 0.0079 |
| 3 | 16.0 | 38.8 | 27.1 | 17.7 | 0.18 | 812 | 2430 | 2.23 | 541 | 0.0033 |
| 4 | 13.1 | 38.3 | 35.2 | 13.2 | 0.04 | 817 | 2281 | 1.20 | 342 | 0 |

EXAMPLE 3

Seven runs are carried out in a 1.83 liter Hastelloy B-2 autoclave fitted with Hastelloy B-2 baffles. Mixing is provided by a Teflon-coated magnetic stirring bar operated at about 630 rpm. Provisions for obtaining liquid samples of the reaction mixture under the reaction conditions consist of a Hastelloy B-2 dip tube equipped with the necessary valve system to permit safe removal of liquid under pressure. The temperature of the reaction mixture is monitored by an iron constantan thermocouple placed in a thermowell immersed in the liquid. Constant pressure is maintained throughout each run. The solid catalyst components and the liquid reactants are placed in the autoclave. After sealing and pressure testing, the mixture is flushed with CO by pressurizing to 100 psig with stirring followed by slowly venting to atmospheric pressure. After a second pressurization-vent cycle, the autoclave is pressurized to 10 psig with the reactant gas and then heated to the desired temperature. An aliquot of the reaction mixture taken at this point is used as a zero time sample. Immediately following the initial sampling, the autoclave is pressurized to the desired value with the reactant gas. The course of the reaction is followed by removing aliquots of the reaction mixture at 30 minute intervals while maintaining reaction conditions. To ensure representative sampling, the second of two 5-ml aliquots taken at the specified sampling time is used to obtain analytical data.

The aliquot samples are cooled and analyzed directly by gas chromatography (10% OF-1, $\frac{1}{8}''\times 8'$, Ni, 100/120 CW-HP) using butyronitrile as an internal standard. Data for each sample are obtained in terms of milligrams of component per gram of solution. Based on the assumption that the weight increase of the reaction mixture during the experiment is due only to the weight of CO used to produce acetic anhydride (Ac$_2$O) the following formula is used to calculate the total moles of acetic anhydride present at the sampling time.

$$\text{MOLES}_{Ac_2O} = \left[ \frac{W_o}{1 - \frac{28}{102} X_{Ac_2O}} \right] \frac{X_{Ac_2O}}{102}$$

$W_o$ = initial weight of reaction mixture $$X_{Ac_2O} = \frac{\text{mg } Ac_2O}{\text{gm Solution}} \times 10^{-3}$$

Runs 1 and 2 are carried out at 175° C. and 650 psig using (1) a gas feed of carbon monoxide without hydrogen and carbon monoxide containing 5 volume percent and (2) the following materials:

| | |
|---|---|
| RhCl$_3$.xH$_2$O | 1.24 g. |
| LiI | 33.85 g. |
| HOAc | 220.50 g. |
| CH$_3$OAc | 676.50 g. |
| CH$_3$I | 130.20 g. |

Runs 3 and 4 are conducted at 190° C. and 1000 psig, with and without hydrogen in the carbon monoxide feed using the following materials:

| | |
|---|---|
| RhCl$_3$.xH$_2$O | 0.62 g. |
| LiI | 25.39 g. |
| HOAc | 220.50 g. |
| CH$_3$OAc | 676.50 g. |
| CH$_3$I | 130.20 g. |

In each of Runs 5, 6 and 7, 0, 5 and 10 volume percent hydrogen is present in the carbon monoxide fed to the autoclave. These runs are carried out at 200° C. and 1000 psig using the following materials:

| | |
|---|---|
| RhCl$_2$.xH$_2$O | 0.30 g. |
| LiI | 12.30 g. |
| HOAc | 220.50 g. |
| CH$_3$OAc | 676.50 g. |
| CH$_3$I | 130.20 g. |

The results, shown in Table III, obtained from Runs 1–7 show that the inclusion of hydrogen in the carbon monoxide used to carbonylate methyl acetate increases substantially the rate at which acetic anhydride is formed. Runs 6 and 7 further show that the use of 10 volume percent hydrogen in the carbon monoxide does not increase the rate over that observed when 5 volume percent hydrogen is used.

TABLE III

| Time, minutes | Run 1 No H$_2$ | Run 2 5% H$_2$ | Run 3 No H$_2$ | Run 4 5% H$_2$ | Run 5 No H$_2$ | Run 6 5% H$_2$ | Run 7 10% H$_2$ |
|---|---|---|---|---|---|---|---|
| 30 | 0.41 | 0.75 | 0.57 | 1.08 | 0.44 | — | 0.84 |
| 60 | 1.07 | 2.06 | 1.61 | 2.30 | 1.28 | 1.56 | 1.70 |
| 90 | 1.75 | 3.05 | 2.60 | 3.42 | 1.95 | 2.30 | 2.47 |
| 120 | 2.40 | 4.10 | 3.48 | 4.36 | 2.49 | 3.10 | 3.20 |
| 150 | 3.25 | 4.85 | 4.35 | 5.36 | 3.04 | 3.90 | 3.96 |
| 180 | 3.91 | 5.47 | 4.98 | 6.07 | 3.57 | 4.43 | 4.50 |
| 210 | 4.44 | 6.27 | 5.63 | 6.80 | 3.87 | 4.94 | 5.06 |
| 240 | 5.03 | 6.74 | 6.00 | 7.25 | 4.31 | 5.83 | 5.72 |
| 270 | 5.60 | 7.25 | 6.55 | 7.43 | 4.68 | 6.15 | 6.20 |
| 300 | 6.10 | 7.56 | 6.82 | 7.88 | — | — | — |

EXAMPLE 4

A 300 cc Hastelloy B-2 Magnedrive autoclave is fitted with a dip tube and the necessary valve system to permit safe removal of liquid under pressure. The following are charged to the autoclave: RhCl$_3$.xH$_2$O, 0.95 g; LiI, 13.0 g; CH$_3$I, 6.10 g; HOAc, 40.0 g; CH$_3$OAc, 144.0 g. The autoclave is sealed, pressure tested, and flushed with carbon monoxide as in Example 3. The autoclave is pressurized to 10 psig with carbon monoxide and heated to 175° C. After pressurizing to 800 psig with carbon monoxide, samples are taken at 20 minute intervals. Immediately following the sampling at 120 minutes, the autoclave pressure is raised from 800 psig to 1,000 psig by the addition of hydrogen. The total pressure is then allowed to drop to 800 psig before additional carbon monoxide is added to maintain 800 psig total pressure. The results, shown in Table IV, show that the addition of $H_2$ substantially increases the rate of production of $Ac_2O$.

TABLE IV

| Time, (Min.) | $Ac_2O$ (Moles) |
|---|---|
| 20 | 0.06 |
| 40 | 0.08 |
| 60 | 0.13 |
| 80 | 0.19 |
| 100 | 0.26 |
| 120* | 0.31 |
| 140 | 0.53 |
| 160 | 0.76 |
| 180 | 0.97 |
| 200 | 1.12 |
| 220 | 1.25 |

*$H_2$ added immediately after sample was taken.

The invention has been described in detail with particular reference to certain preferred embodiments thereof, but it will be understood that variations and modifications can be effected within the spirit and scope of the invention.

We claim:

1. In a process for the preparation of acetic anhydride by the carbonylation of methyl acetate in the presence of rhodium and an iodine compound at elevated pressure and temperature, the improvement comprising the presence of about 2 to 7 volume percent hydrogen in the gas fed to the carbonylation reactor and the carbonylation is carried out in the presence of lithium.

2. The process of claim 1 wherein about 3 to 6% hydrogen is present in the gas.

3. Process for the preparation of acetic anhydride which comprises carbonylating in the liquid phase methyl acetate in the presence of about 250 to 1300 ppm. rhodium, about 175 to 5000 ppm. lithium and methyl iodide at a temperature of about 160° to 220° C. and about 300 to 1200 psig wherein about 2 to 7 volume percent of the gas fed is hydrogen.

4. Process for the preparation of acetic anhydride by the liquid phase carbonylation of methyl acetate in the presence of rhodium, methyl iodide and lithium at a temperature of about 160° to 220° C. and about 300 to 1200 psig wherein a feed mixture containing methyl acetate is continuously fed to a carbonylation reactor and a reaction mixture containing acetic anhydride is continuously removed, the feed to the reactor is such as to maintain within the reaction mixture (1) about 500 to 1000 ppm. rhodium, (2) about 1500 to 3700 ppm. lithium, (3) about 7 to 35 weight percent methyl iodide and (4) about 5 to 40 weight percent acetic acid; wherein about 3 to 6 volume percent of the gas fed to the reactor is hydrogen.

* * * * *